(12) United States Patent
Cabri et al.

(10) Patent No.: US 9,586,919 B2
(45) Date of Patent: Mar. 7, 2017

(54) CRYSTALLINE ANHYDROUS FORM OF CABAZITAXEL, PROCESS FOR THE PREPARATION AND PHARMACEUTICAL COMPOSITIONS THEREOF

(71) Applicant: INDENA S.P.A., Milan (IT)

(72) Inventors: Walter Cabri, Milan (IT); Daniele Ciceri, Milan (IT); Luca Domenighini, Milan (IT); Andrea Gambini, Milan (IT); Federico Peterlongo, Milan (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 15/030,620

(22) PCT Filed: Oct. 9, 2014

(86) PCT No.: PCT/EP2014/071601
§ 371 (c)(1),
(2) Date: Apr. 20, 2016

(87) PCT Pub. No.: WO2015/058961
PCT Pub. Date: Apr. 30, 2015

(65) Prior Publication Data
US 2016/0244420 A1  Aug. 25, 2016

(30) Foreign Application Priority Data
Oct. 23, 2013  (EP) ..................................... 13189949

(51) Int. Cl.
*C07D 305/14* (2006.01)

(52) U.S. Cl.
CPC ........ *C07D 305/14* (2013.01); *C07B 2200/13* (2013.01)

(58) Field of Classification Search
None
See application file for complete search history.

(56) References Cited

U.S. PATENT DOCUMENTS

2013/0178639 A1*  7/2013  Billot ................... C07D 305/14
                                                           549/510

FOREIGN PATENT DOCUMENTS

| WO | 2009115655   | * | 9/2009 |
|----|--------------|---|--------|
| WO | 2009115655 A2 |   | 9/2009 |

OTHER PUBLICATIONS

Search Report and Writtein Opinion of PCT/EP2014/071601 of Dec. 23, 2014.

* cited by examiner

*Primary Examiner* — Karl J Puttlitz
(74) *Attorney, Agent, or Firm* — Silvia Salvadori, P.C.; Silvia Salvadori

(57) ABSTRACT

The present invention relates to a new anhydrous crystalline form of Cabazitaxel of formula (I), designated as form H. A further object of the present invention is a processes for the preparation of the above mentioned form H by recrystallization of Cabazitaxel from a mixture of decanoyl- and octanoyl triglycerides or from glycerol trioctanoate. Form H of Cabazitaxel is useful for the preparation of Cabazitaxel, Cabazitaxel salts, and polymorphic forms thereof. It is also particularly useful as a medicament, especially for the treatment of cancers.

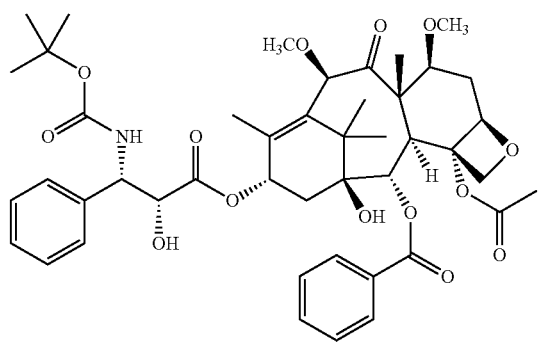

3 Claims, 4 Drawing Sheets

CRYSTALLINE ANHYDROUS FORM OF CABAZITAXEL, PROCESS FOR THE PREPARATION AND PHARMACEUTICAL COMPOSITIONS THEREOF

This application is a U.S. national stage of PCT/EP2014/071601 filed on 9 Oct. 2014, which claims priority to and the benefit of European Application No. 13189949.4 filed on 23 Oct. 2013, the contents of which are incorporated herein by reference in their entireties.

FIELD OF THE INVENTION

The present invention relates to a new crystalline anhydrous form of Cabazitaxel, to a process for its preparation and to pharmaceutical compositions thereof.

BACKGROUND OF THE INVENTION

Cabazitaxel is a semi-synthetic derivative of the natural taxoid 10-deacetylbaccatin III, commercialized as acetone solvate. It stabilizes microtubules leading eventually to the mitotic arrest of proliferating cells. It has been approved in the United States of America for the second line treatment of hormone-refractory prostate cancer following a docetaxel-based treatment.

Cabazitaxel has the following formula (I):

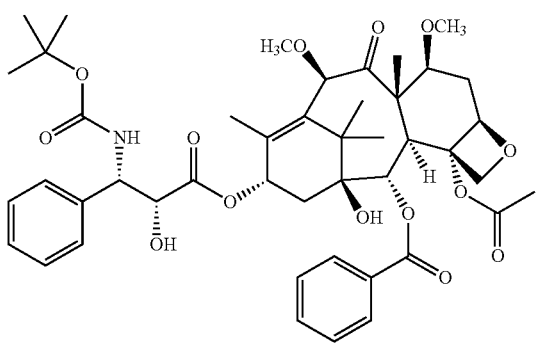

Its chemical name is 4α-acetoxy-2α-benzoyloxy-5β-epoxy-1β-hydroxy-7β, 10β-dimethoxy-9-oxo-11-taxen-13α-yl (2R,3S)-3-tert-butoxycarbonylamino-2-hydroxy-3-phenylpropionate.

Cabazitaxel and methods for the preparation thereof are described in WO96/30355 and in WO99/25704.

WO2005/028462 describes an acetone solvate of Cabazitaxel, sometimes referred to as form A. Despite the fact that crystallisation of the acetone solvate is a very effective way for removing impurities, a better pharmaceutical form will be pure Cabazitaxel without any crystallization solvent.

Additional crystalline solvate forms of Cabazitaxel referred to as form I (toluene solvate), form II (methyl tert-butyl ether solvate), form III (2-propanol solvate), form IV (1-butanol solvate), form V (1-propanol solvate) and an amorphous form of Cabazitaxel in a powdery, non-foamy form are described in WO2012/142117 (Teva). Solvates are rarely used in pharmaceuticals because the solvents are volatile thus making it difficult to maintain the solvent in the crystal. If the API desolvates due to storage conditions or otherwise, it could lead to the formation of multiple polymorphs with different physical properties. Additionally, amorphous solids are metastable and can lead with time to the formation of different polymorphs with different physical properties.

WO2009/115655 (Sanofi) discloses five anhydrous forms of the compound, referred to as forms B, C, D, E and F; three ethanol solvates, referred to as ethanolate forms B, D, E; an ethanol/water heterosolvate form F; and a monohydrate-solvent free form C and a dihydrate-solvent free form C. Reaching high purities with these forms is only possible providing the API has been previously purified by other techniques such as for example passing through the acetone solvate (as described in the application). However the introduction of a further purification technique hampers the manufacturing process with inefficiency due to longer production times and lower yield.

WO 2013/134534 discloses crystalline Cabazitaxel solvates with:
  alkyl acetates, such us the solvates with ethyl acetate (Form VII), isopropyl acetate (Form VIII), methyl acetate (Form XVII), butyl acetate (Form XVIII) and isobutyl acetate (Form XXI);
  ketones, such as the solvates with methyl ethyl ketone (Form IX) and methyl isobutyl ketone (Form X);
  alcohols, such as the solvates with 2-butanol (Form XI), isobutanol (Form XII) and amyl alcohol (Form XIII).

WO 2013/134534 also describes solvates with dioxolane (Form XIV), 1,4-dioxane (Form XV), 1,2-propanediol (Form XIX), glycerol (Form XX) and 1,3-dimethy-2-imidazolidinone (Form XXII). A crystalline Cabazitaxel form designated as Form XVI, which may be anhydrous, is also disclosed.

A crystalline ethyl acetate solvate of Cabazitaxel is disclosed also in WO 2013/088335.

WO2009/115655 discloses two hydrate forms of the compound in particular mono and di-hydrate, both hydrate forms are obtained from anhydrous form C by exposition to moisture. The anhydrous form C as described above is obtained in high purity only by passing through the acetone solvate.

A crystalline form of Cabazitaxel obtained from acetone/water is described in CN 102675257 A.

Crystalline forms, including an anhydrate form, of Cabazitaxel, designated as Forms C1, C2, C3, C4, C5, C6, C7, C8, C8b, C9 and C9p are described in WO2013/034979.

Finally, 13 crystalline forms referred to as Form-1, Form-2, Form-3, Form-4, Form-5, Form-6, Form-7, Form-8, Form-9, Form-10, Form-11, Form-12, and Form-13 are disclosed in WO2013/0109870.

It is still desirable to find new crystalline forms able to solve the aforementioned problems.

BRIEF DESCRIPTION OF THE INVENTION

Object of the present invention is a new anhydrous crystalline form of Cabazitaxel, designated as form H. A further object of the present invention are processes for the preparation of the above mentioned crystalline form and pharmaceutical compositions thereof.

In the present invention the term "anhydrous" refers to a crystalline form of Cabazitaxel which contains less than 1% of adsorbed moisture as determined by Karl Fisher analysis.

Form H is an anhydrous crystalline form of Cabazitaxel obtained crystallizing Cabazitaxel from a mixture of decanoyl- and octanoyl triglycerides (CAS number 52622-27-2), known under the trade name Miglyol® 812, or from glycerol trioctanoate.

DETAILED DESCRIPTION OF THE INVENTION

Figure 1:
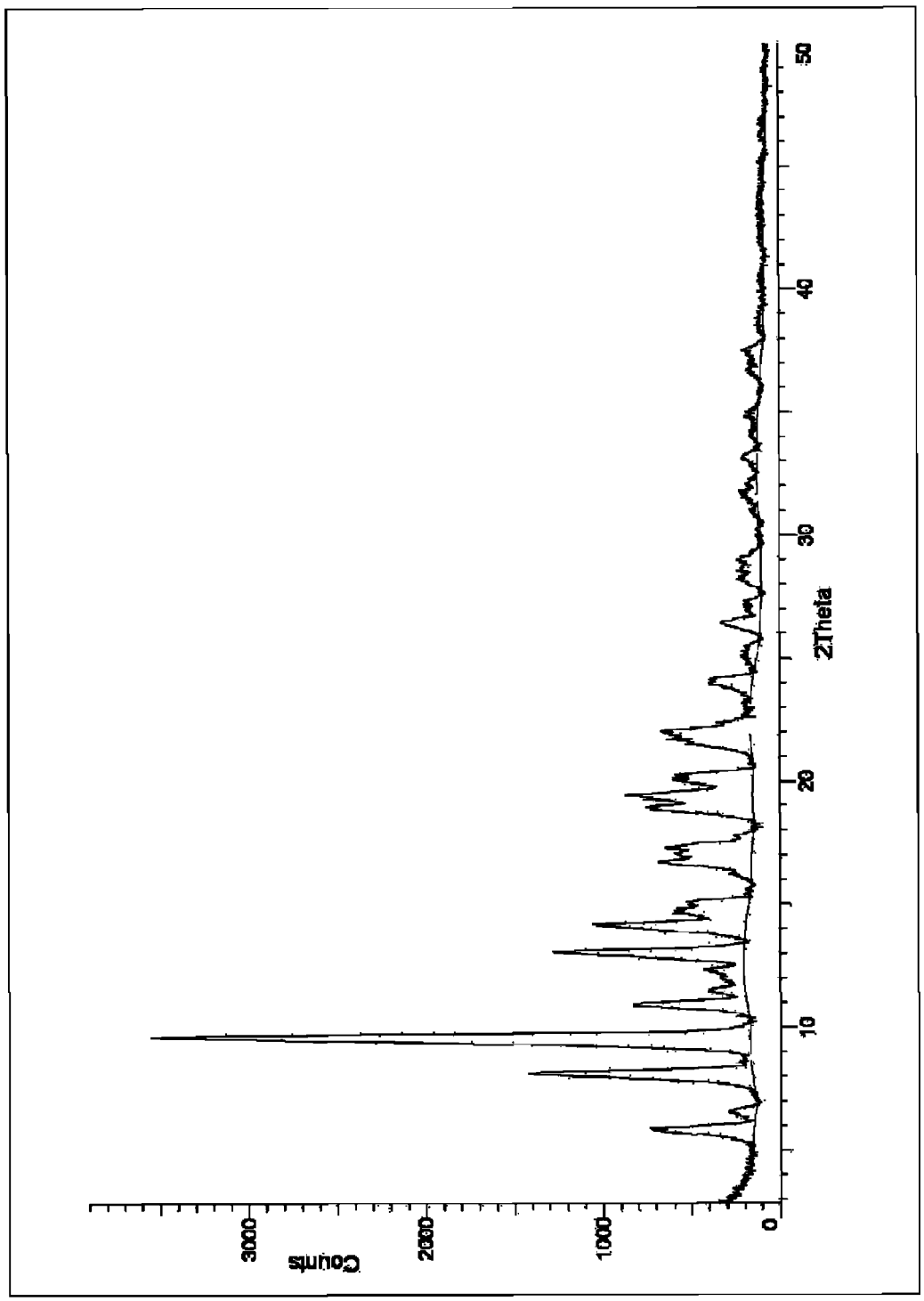
FIG. 1 X-RPD pattern of the crystalline form H of Cabazitaxel

Form H of Cabazitaxel according to the present invention is characterised by a x-ray powder diffraction (X-RPD) pattern obtained using the copper wavelengths $\lambda_1$ and $\lambda 2$ of 1.54056 Å and 1.54439 Å, respectively, essentially as depicted in FIG. 1. The X-RPD pattern shows a crystalline structure and comprises distinctive reflections, expressed as 2-theta degrees values, at 5.8, 6.5, 8.1, 9.5, 10.9, 11.5, 12.2, 13.0, 14.1, 14.8, 16.8, 17.2, 19.0, 19.4, 20.1, 21.9 and 24.0±0.2.

The X-RPD pattern as depicted in FIG. 1 was indexed by TOPAS with an orthorhombic cell and possible space group $P2_12_12_1$. A Pawley refinement converged to a Rwp=7.065% with the following cell parameters: a=18.693(4) Å, b=27.461(5) Å, c=8.587(1) Å, $\alpha=\beta=\gamma=90°$, V=4408(1) Å$^3$ and space group $P2_12_12_1$, coherent with the presence of 4 molecules in the cell.

Figure 2:
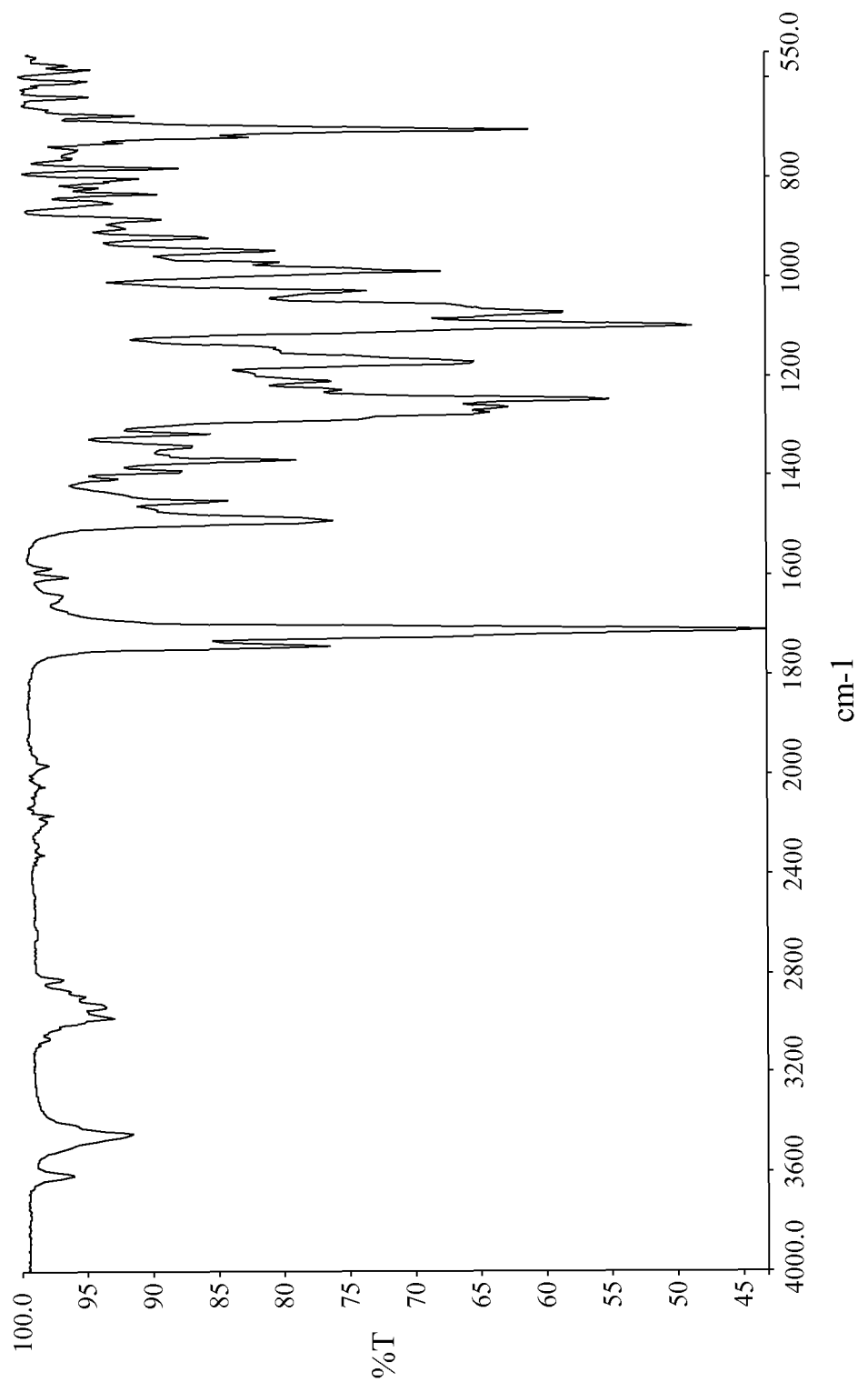
FIG. 2 FTIR spectrum of the anhydrous crystalline form H of Cabazitaxel in the 4000-550 cm$^{-1}$ spectral range FIG. 3 TG and DTA profiles of the anhydrous crystalline form H of Cabazitaxel FIG. 4 DSC profile of the anhydrous crystalline form H of Cabazitaxel

Form H may be further characterised by a Fourier-Transform InfraRed Spectroscopy (FTIR) spectrum in the 4000-550 cm$^{-1}$ spectral range in ATR mode essentially as depicted in FIG. 2. The FTIR spectrum of form H comprises characteristic absorption frequencies at 3615, 3449, 3060, 2982, 2939, 2893, 2826, 1742, 1711, 1489, 1450, 1390, 1368, 1315, 1273, 1263, 1247, 1172, 1098, 1071, 1027, 989, 947, 919, 883, 832, 802, 781, 718, 704, 675 and 637±4 cm$^{-1}$.

Figure 3:
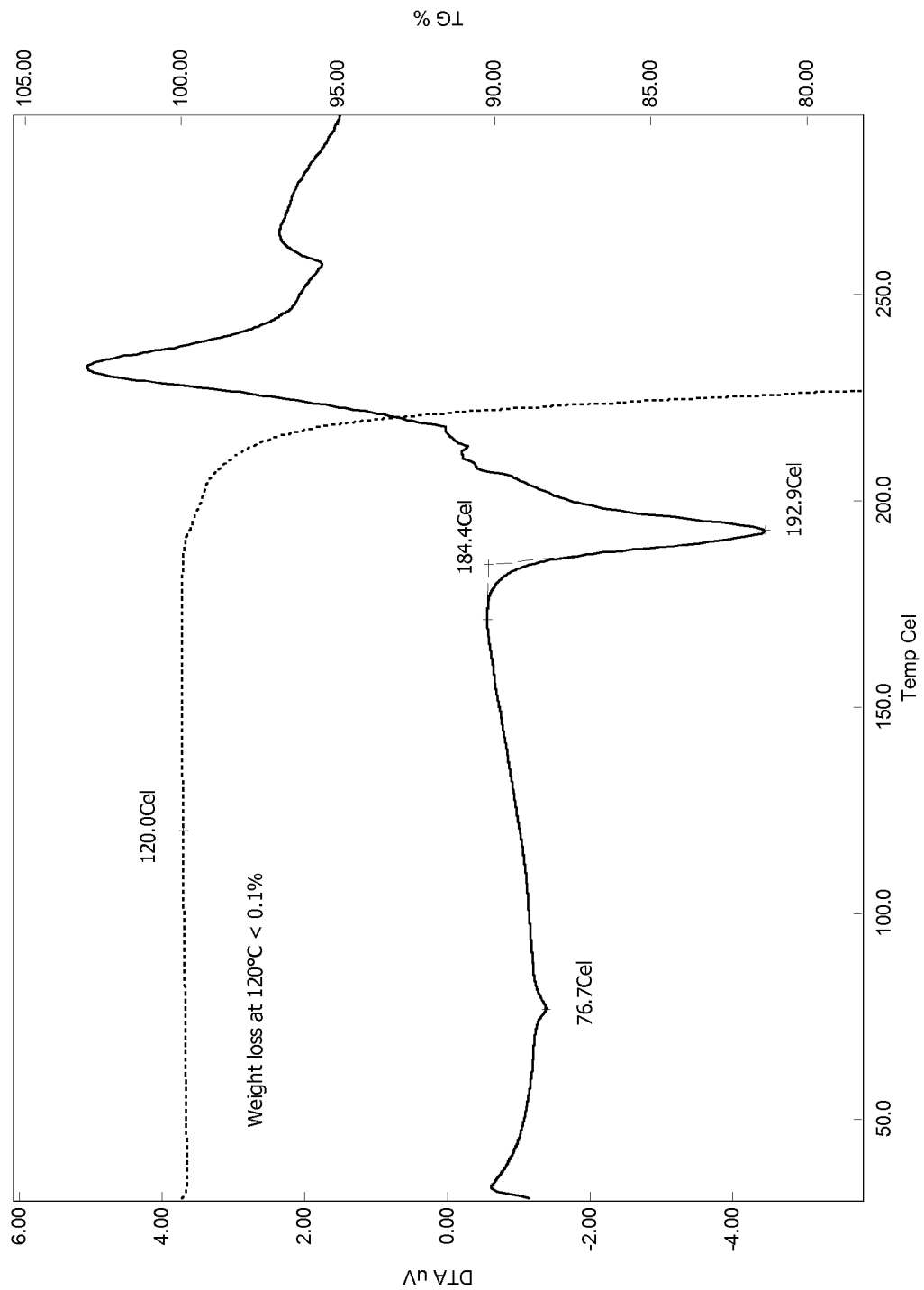

Form H may be further characterised by Thermogravimetric (TG) and Differential Thermal Analysis (DTA) profiles as depicted in FIG. 3. The DTA profile is characterised by a melting peak with onset at about 184° C. and maximum at 192.9° C. followed by an intense exothermic peak due to decomposition.

In the TG profile, the absence of weight loss until melting is coherent with an anhydrous product, free of residual solvents.

Figure 4:
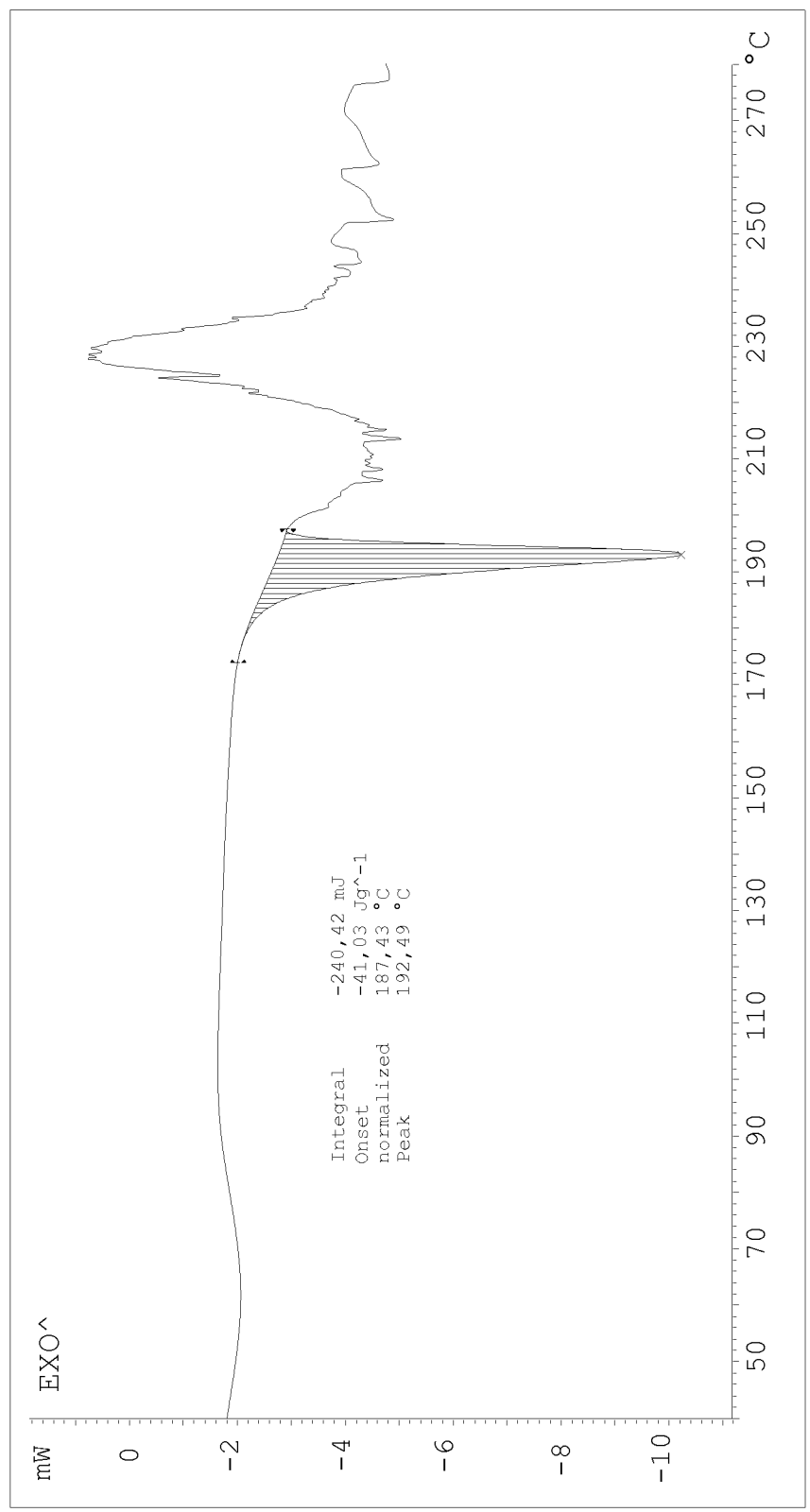

Form H may be further characterised by a DSC profile as depicted in FIG. 4. The DSC profile is coherent with the DT signal and shows a thermal profile characterised by a melting peak with onset at 187.4° C., maximum at 192.5° C., and ΔH=−41.03 J/g, followed by decomposition which takes place above 200° C.

When the crystalline form of Cabazitaxel according to the present invention is referred to herein as being characterized by graphical data essentially as depicted in a figure, such as for, for example, the X-RPD diffractogram, the TG/DTA, DSC profiles and the FTIR spectrum, the skilled person will understand that such graphical representations of data may be affected by small variations which may be triggered by experimental variability affecting the instrumental response and/or the sample concentration and purity. These variations are well known to the skilled person and they will not prevent him from comparing the graphical data in the figures herein with graphical data generated for an unknown crystal form and from assessing whether the two sets of graphical data are characterizing the same crystal form or two different crystal forms.

The anhydrous crystalline form H of Cabazitaxel of the present invention may be prepared starting from a solution of Cabazitaxel in a mixture of decanoyl- and octanoyl triglycerides or in glycerol trioctanoate, as described in Example 1 or 2, respectively. Precipitation of the crystals of the anhydrous form H occurs spontaneously and may be completed by the-addition of an anti-solvent such as heptane. The obtained crystals are then recovered by filtration, washed with fresh anti-solvent and dried.

A further object of the invention is therefore a process for the preparation of the crystalline anhydrous form H of Cabazitaxel comprising the following steps:
 a) dissolution of Cabazitaxel in a mixture of decanoyl- and octanoyl triglycerides or in glycerol trioctanoate at 20-25° C.;
 b) stirring of the solution obtained in step a), wherein a product starts to crystallize;
 c) addition of heptane to the slurry obtained in step b);
 d) filtration and drying of the precipitate obtained in step c), to afford the crystalline form H of Cabazitaxel.

The crystalline anhydrous form H of the invention may be obtained with purity higher than 99% when obtained as described in the examples 1-2.

The anhydrous crystalline form of the invention is endowed with several advantageous properties as compared to the previously disclosed forms of Cabazitaxel in term of, for example, high purity obtainable without the need of an additional crystallization, stability to conversion to other polymorphic forms, better handling and improved processability.

In view of the above described advantages, the anhydrous crystalline form H of Cabazitaxel of the invention is useful for the preparation of Cabazitaxel, Cabazitaxel salts, and polymorphic forms thereof In addition, the anhydrous crystalline form H of the invention is particularly useful as a medicament, especially for the treatment of cancers and, in particular, of prostate cancers such as, for example, hormone-resistant prostate cancer.

The above uses of the anhydrous crystalline form H of Cabazitaxel represent a further object of the invention.

For the therapeutic uses, the anhydrous crystalline form H of the invention may be incorporated in conventional pharmaceutical compositions containing at least one excipient suitable for the pharmaceutical uses, which represent a further object of the invention.

The invention is now further illustrated by the following examples, wherein a crude Cabazitaxel was used as starting material.

EXAMPLE 1

Preparation of Anhydrous Crystalline form H of Cabazitaxel by Miglyol® 812 Recrystallization of Crude Cabazitaxel Crude Cabazitaxel (1 g) was dissolved in Miglyol® 812 (28 g) at room temperature. The solution was left to crystallized then heptane (112 mL) was added. The precipitate was filtered, washed with heptane and dried under vacuum for 16 hours at about 60° C. Cabazitaxel with purity higher than 99% was obtained. Yield 85%.

EXAMPLE 2

Preparation of Anhydrous form H of Cabazitaxel by Glycerol Trioctanoate Recrystallization of Crude Cabazitaxel Crude Cabazitaxel (1 g) was dissolved in glycerol trioctanoate (28 g) at room temperature. The solution was left to crystallize then heptane (112 mL) was added. The precipitate was filtered, washed with heptane and dried under vacuum for 16 hours at about 60° C. Cabazitaxel with purity higher than 99% was obtained. Yield 84%.

EXAMPLE 3

The compound obtained according to Examples 1-2 was characterized using the below described techniques.

X-Ray Powder Diffraction (X-RPD) (FIG. 1)

X-RPD patterns were collected on a Bruker D2-Phaser Diffractometer. The x-ray generator was operated at 30 kV and 10 mA, using the CuKα line as the radiation source. The sample was packed on a suitable slit and the irradiated length was 10 mm. Data were collected between 2 and 50 deg 2-theta with a step size of 0.02 deg 2-theta and a counting time per step of 3 sec.

Fourier-Transform InfraRed Spectroscopy (FTIR) (FIG. 2)

The infrared spectrum was recorded in Attenuated Total Reflectance (ATR) mode using Fourier-Transform spectrometer Perkin Elmer Spectrum One, equipped with Specac ATR Golden Gate accessory. The spectrum is the result of the acquisition and transformation of 16 co-added scans in the 4000-550 cm$^{-1}$ spectral region at a resolution of 4 cm$^{-1}$.

Thermogravimetry (TG) and Differential Thermal Analysis (DTA) (FIG. 3)

The analysis was performed using a Seiko TG/DTA7200 simultaneous system using open aluminum pans (40 μl volume). The TG/DT signals were recorded from 30 to 300° C. with linear heating rate (10° C./min) under a 200 ml/min nitrogen flow. About 10 mg of powder was used for the measurement.

Differential Scanning Calorimetry (DSC) (FIG. 4)

The analysis was performed using a Mettler DSC1 System. Heat flow was recorded from 30 to 300° C. with linear heating rate (10° C./min) under a 50 ml/min nitrogen flow. About 5 mg of powder was used for the measurement, in closed aluminum crucible (40 μl volume) with a pinhole.

The invention claimed is:

1. An anhydrous crystalline form, referred to as form H, of Cabazitaxel of formula (I)

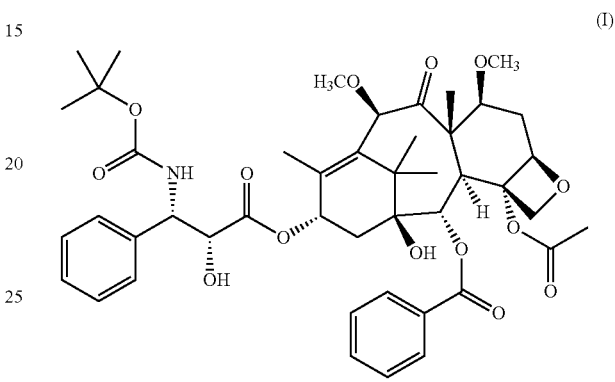

(I)

wherein the anhydrous crystalline form has
an X-RPD pattern obtained using the copper wavelengths $\lambda_1$ and $\lambda_2$ of 1.54056 Å and 1.54439 Å, respectively, comprising distinctive reflections, expressed as 2-theta degrees values, at 5.8, 6.5, 8.1, 9.5, 10.9, 11.5, 12.2, 13.0, 14.1, 14.8, 16.8, 17.2, 19.0, 19.4, 20.1, 21.9 and 24.0±0.2.

2. Pharmaceutical compositions comprising the anhydrous crystalline form H according to claim 1 in admixture with at least one pharmaceutically suitable excipient.

3. A process for the preparation of the anhydrous crystalline form H according to claim 1, comprising:
dissolving Cabazitaxel in a decanoyl- and octanoyl-triglycerides or glycerol trioctanoate to form a mixture;
adding heptane to said mixture;
filtering said mixture to obtain crystals of said form H.

* * * * *